(12) United States Patent
Kong et al.

(10) Patent No.: US 6,867,339 B2
(45) Date of Patent: Mar. 15, 2005

(54) PROCESS FOR PRODUCING P-XYLENE

(75) Inventors: Dejin Kong, Shanghai (CN); Weisheng Yang, Shanghai (CN); Hongli Guo, Shanghai (CN); Huaying Li, Shanghai (CN)

(73) Assignees: China Petroleum & Chemical Corporation, Bejing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 125 days.

(21) Appl. No.: 10/391,890

(22) Filed: Mar. 19, 2003

(65) Prior Publication Data
US 2004/0186330 A1 Sep. 23, 2004

(51) Int. Cl.$^7$ ................................................ C07C 15/08
(52) U.S. Cl. ...................... 585/319; 585/470; 585/475; 585/479
(58) Field of Search ................. 585/319, 470, 585/475, 474

(56) References Cited

U.S. PATENT DOCUMENTS

| | | |
|---|---|---|
| 2,795,629 A | 6/1957 | Boedeker |
| 3,551,510 A | 12/1970 | Pollitzer et al. |
| 4,341,914 A | 7/1982 | Berger |

FOREIGN PATENT DOCUMENTS

| | | |
|---|---|---|
| CN | 1217369 | 5/1999 |
| CN | 235948 | 11/1999 |

*Primary Examiner*—Thuan Dinh Dang
(74) *Attorney, Agent, or Firm*—Cohen, Pontani, Lieberman & Pavane

(57) ABSTRACT

A complete new process for producing p-xylene is provided to solve the problems in the prior arts of the great amount of benzene as a by-product and the requirement of low content of $C_{10}^+$ heavy aromatics in the feedstock. The process comprises first subjecting benzene and $C_9^+$ aromatics to alkyl transfer reaction to produce toluene and $C_8$ aromatics, then conducting toluene selective disproportionation, and molecular sieve adsorptive separation and isomerization of $C_8$ aromatics, to obtain p-xylene.

15 Claims, 3 Drawing Sheets

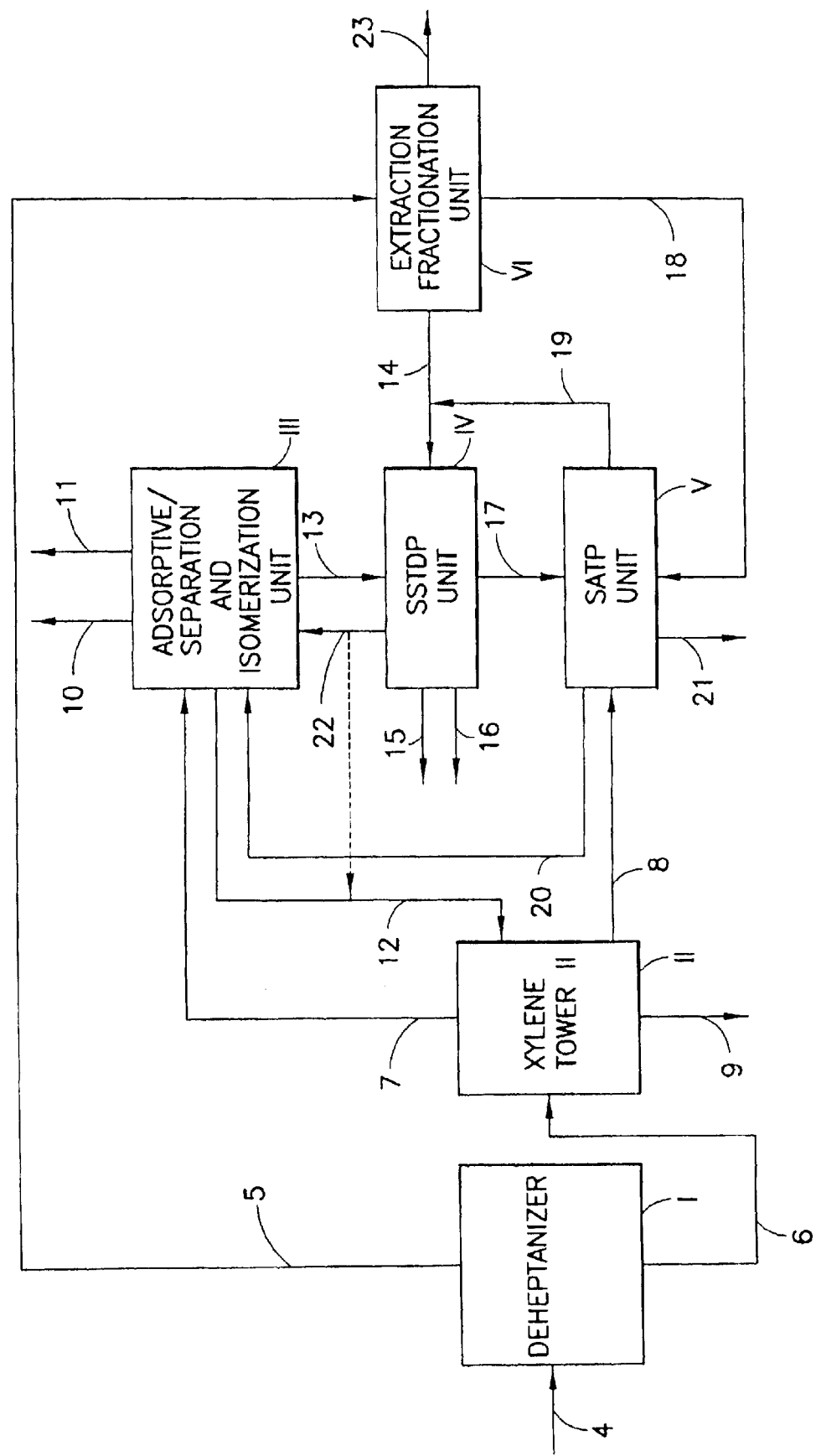

PROCESS FOR PRODUCING P-XYLENE

FIELD OF THE INVENTION

The present invention relates to a process for producing p-xylene (pX). In particular it is a process for producing p-xylene wherein a great amount of toluene (Tol) and $C_8$ aromatics ($C_8A$) is first produced via the alkyl transfer reaction between benzene (Ben) and $C_9^+$ aromatics ($C_9^+A$), and then p-xylene is produced via the selective disproportionation of toluene, molecular sieve adsorptive separation and $C_8A$ isomerization.

BACKGROUND OF THE INVENTION p-xylene is one of the major basic organic feedstocks in petrochemical industry and has widespread applications in many fields such as chemical fiber, synthetic resin, pesticide, medicine, plastic, etc. The typical process for producing p-xylene (pX) is to separate p-xylene in the xylene stream containing ethylbenzene, i.e. $C_8$ aromatics in thermodynamic equilibrium produced in the catalytic reforming of naphtha by multi-stage cryogenic crystallization separation or molecular sieve simulation moving bed separation (abbreviated as adsorptive separation) from its isomer mixture with near boiling points. A $C_8A$ isomerization (abbreviated as isomerization) process is generally used to isomerize o-xylene and m-xylene to p-xylene. The use of disproportionation of toluene, or the disproportionation and alkyl transfer reaction of toluene and $C_9^+$ aromatics ($C_9^+A$) to produce benzene and $C_8A$, and thereby increase the output of $C_8A$ is an effective route for increasing the output of p-xylene.

So far, the rather typical and mature processes relating to toluene disproportionation in the world include the Tatoray traditional toluene disproportionation process industrialized in the end of 1960s, the MTDP process developed in the end of 1980s, and the S-TDT and TransPlus processes developed in recent years. The selective disproportionation of toluene is a new route for producing p-xylene. Since the selective disproportionation of toluene on modified ZSM-5 catalysts can produce benzene and $C_8A$ with a high concentration of p-xylene, only one simple step of cryogenic separation is enough for separating most of the highly pure p-xylene. In recent years, along with the improvement of the catalyst performance, this process has made a great progress. The typical processes include the MSTDP selective disproportionation process of toluene industrialized late 1980s and the pX-Plus process developed in recent years.

In the industrialized toluene selective disproportionation process-MSTDP, a treated ZSM-5 mesoporous molecular sieve is used as the catalyst to treat a toluene feedstock yielding $C_8A$ with a high concentration of p-xylenes (85–90% by weight, the same bellow except otherwise noted) and nitration grade benzene. In the pX-Plus process, the report on the industrialization of which has not seen, the major indices are a pX selectivity of 90% and a benzene/pX mole ratio of 1.37 in case of a toluene conversion of 30%.

However, in this kind of processes for toluene selective disproportionation, a high p-xylene selectivity is accompanied by a harsh requirement for the feedstock selection, and only toluene can be used as the feedstock, while $C_9^+A$ has no use for this kind of processes, and at least it cannot be directly used. Besides, this process also produces a great amount of benzene as a by-product, resulting in a low yield of p-xylene. This is a vital shortcoming of the process for selective disproportionation.

The feed to the reactor of the typical Tatoray process is toluene and $C_9$ aromatics ($C_9A$), and the content of $C_{10}^+$ hydrocarbons ($C_{10}$ and higher hydrocarbons) must be strictly controlled. To increase the economic benefit of the device and decrease the energy and material consumption, further study and optimization of the Tatoray process have been carried out with the focus placed on the kernel technique—the preparation of the catalyst, the improvement of the whole performance of the catalyst such as the increase of the weight space velocity, the elongation of the operation cycle of the catalyst, and the increase of the average molecular weight of the aromatics feedstock. The increase of the average molecular weight benefits the increase of $C_8A$, but in order to maintain a certain conversion, i.e. a certain catalyst activity, too high a content of heavy aromatics would certainly lead to an enhancement of the side-reactions especially the hydrodealkylation reaction, thereby lead to the increase of the benzene product in the reaction product, the decrease of the $C_8A/Ben$ ratio, more loss of aromatics, and therefore lead to less $C_8A$ and more Ben when the same feedstock is treated. The reason why the toluene disproportionation unit is necessary for an aromatics integrated device is that it has a function to provide $C_8A$. The increase of Ben and the decrease of $C_8A$ are obviously unfavorable to the whole aromatics integrated device. These shortcomings have already restricted the development of this kind of processes.

The literature based on the Tatoray Process includes U.S. Pat. No. 4,341,914, CN98110859.8, U.S. Pat. No. 2,795,629, U.S. Pat. No. 3,551,510, CN97106719.8, etc. FIG. 1 is the process flow of U.S. Pat. No. 4,341,914, wherein 1 is the xylene tower I, 2 is the heavy aromatics tower, 3 is the reaction zone, 4 is the benzene tower, 5 is the toluene tower, 6 is the xylene tower II, 7 is $C_9A$, 8 is the $C_8^+A$ feedstock, 9 and 10 are toluene, 11 is benzene, 12 and 13 are $C_8A$, 17 and 19 are the streams rich in $C_{10}^+$ hydrocarbons, and 18 is the stream rich in $C_9A$. In this process, although a part of $C_{10}A$ in the reaction product is returned to the reaction zone along with the recycled $C_9A$ (stream 18) to partly make use of the produced $C_{10}A$ by the reaction itself to suppress the production of a greater amount of $C_{10}^+$ hydrocarbons in the reaction, the $C_{10}^+$ hydrocarbons in the $C_8^+A$ feedstock can not be utilized and a part of $C_9A$ in the $C_8^+A$ feedstock is withdrawn from the bottom of the heavy aromatics tower along with $C_{10}^+$ hydrocarbons (stream 19). Due to the limit of the catalyst performance, this process also has a harsh requirement for the selection of the feedstock, i.e. the effluent from the top of the heavy aromatics tower (tower 2)—the $C_9A$ stream (stream 7) must contain less than 1% of indan (IND), thereby resulting in the aforesaid loss of $C_9A$ and only part utilization of $C_{10}A$ produced by the reaction itself, while the $C_{10}^+$ hydrocarbons in the $C_8^+A$ feedstock can not be utilized.

FIG. 2 is the process flow of CN98110859.8, wherein 1 is the xylene tower I, 2 is the heavy aromatics tower, 3 is the reaction zone, 4 is the benzene tower, 5 is the toluene tower, 6 is the xylene tower II, 7 is the o-xylene tower, 8 is the $C_8^+A$ feedstock, 9 is the fresh toluene, 12 and 13 are $C_8A$, 14 is the stream rich in $C_9A$, 15 is $C_{11}$ and higher hydrocarbons ($C_{11}^+$ hydrocarbons), 16 is the recycled toluene, 17 is benzene, 19 is o-xylene, 20 is the $C_9A^+$ containing or not containing o-xylene. Although this process has overcome many shortcomings of the above patent and has the advantages of permission of high contents of indan and $C_{10}^+$ hydrocarbons in the feedstock, etc, the amount of the by-product—benzene is still large.

It is readily seen from summarizing the above processes that all these patents are formed by reasonable modifications of a specific catalyst for toluene disproportionation and alkyl transfer in one or more aspects such as the ability for alkyl transfer of heavy aromatics or the separation scheme of the reaction product, but these modifications have not broken though the limit of the original idea of the Tatoray process. The common shortcomings are that benzene is inevitably produced as a by-product when using toluene or toluene and $C_9^+$A to produce $C_8$A and increase the yield of p-xylene and that the heavy aromatics can not be effectively utilized.

SUMMARY OF THE INVENTION

Hence, one object of the present invention is to provide a completely new and more economic process for producing p-xylene for overcoming the shortcomings present in the prior art of the production of a large amount of benzene as a by-product and the low content of heavy aromatics in the feedstock. The process uses benzene, toluene, and $C_8^+$A as feedstocks to produce p-xylene and greatly lower the production cost via setting up a toluene selective disproportionation (abbreviated as SSTDP) unit and reforming the original toluene disproportionation unit into the aromatics alkyl transfer (abbreviated as SATP) unit. Besides, for a typical aromatics integrated device, the output of p-xylene can be markedly increased in case of the same amount of the feedstock by making full use of the existing device and arts since benzene is also used as a feedstock for producing p-xylene.

The objects of the present invention are realized via the following process for producing p-xylene comprising:

a) separating the depentanized oil rich in benzene, toluene, $C_8$ aromatics, and $C_9^+$ aromatics sequentially into the first stream of benzene, the first stream of toluene, the first stream of $C_8$ aromatics, and the first stream of $C_9^+$ aromatics and non-aromatics, wherein the depentanized oil denotes $C_6^+$ aromatics and non-aromatics;

b) introducing the first stream of toluene and the second stream of toluene from the aromatics alkyl transfer unit into the toluene selective disproportionation unit to conduct the toluene selective disproportionation reaction in the presence of hydrogen to produce the second stream of benzene and the second stream of $C_8$ aromatics rich in p-xylene and withdrawing the highly pure p-xylene product derived by the crystallization separation of $C_8$ aromatics rich in p-xylene;

c) introducing all or a part of the first and the second stream of benzene and the first stream of $C_9^+$ aromatics into the aromatics alkyl transfer unit to conduct the aromatics alkyl transfer reaction in the presence of hydrogen to produce the second stream of toluene and the third stream of $C_8$ aromatics, wherein a part of the second stream of toluene may be withdrawed as product;

d) introducing the first stream of $C_8$ aromatics, the second stream of $C_8$ aromatics after separating p-xylene and the third streams of $C_8$ aromatics into the molecular sieve adsorptive separation and $C_8$ aromatics isomerization units to produce p-xylene.

BRIEF DESCRIPTION OF THE DRAWINGS

FIG. 3 is a flow scheme according to one embodiment of the present invention for selective disproportionation and alkyl transfer to produce p-xylene.

MODE OF CARRYING OUT THE INVENTION

Figure 1:
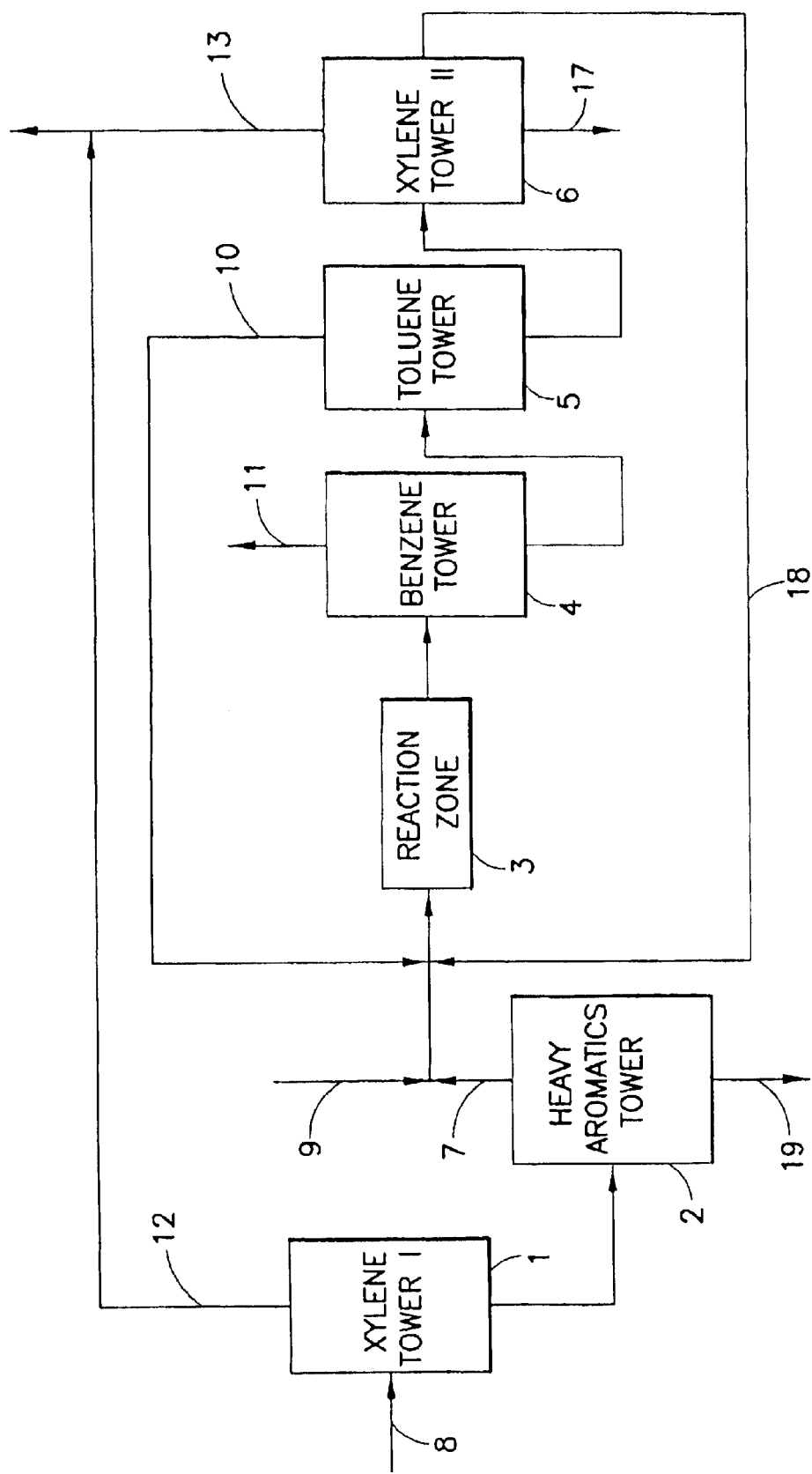
FIG. 1 is a process flow according to U.S. Pat. No. 4,341,914.
Figure 2:
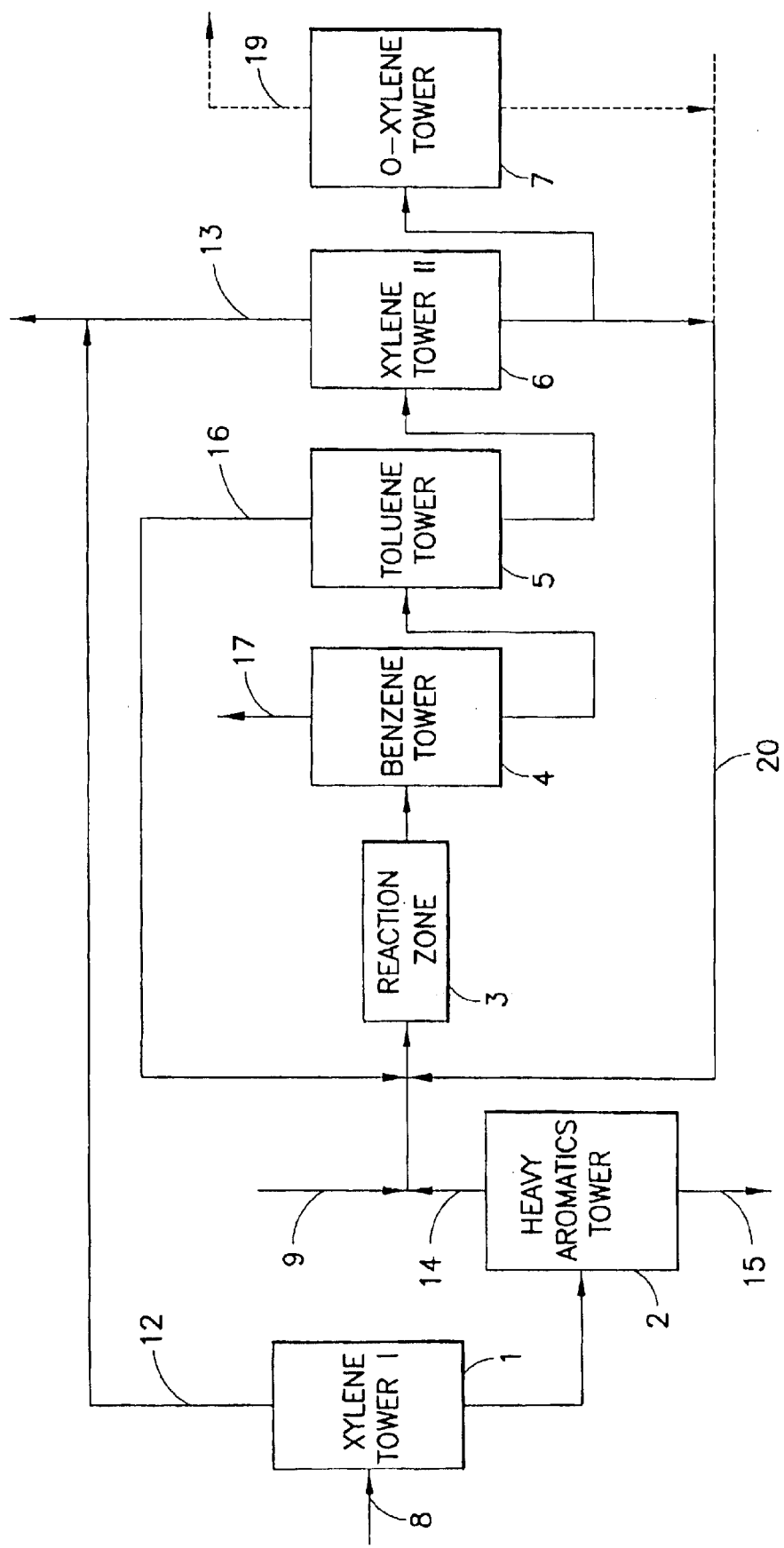
FIG. 2 is a process flow according to Chinese Patent No. CN98110859.8.

In accordance with the present invention, the depentanized oil rich in aromatics can come from the reforming unit; the $C_8$ aromatics rich in p-xylene produced in the toluene selective disproportionation unit can directly enter into the molecular sieve adsorptive separation and $C_8$ aromatics isomerization unit together with the other $C_8$ aromatics after mixing with them without the crystallization separation so that the concentration of p-xylene in the feed to the molecular sieve adsorption separation can be greatly raised and the output of p-xylene in the whole aromatics unit can be increased.

In accordance with the present invention, the first stream of benzene, the first stream of toluene, the first stream of $C_8$ aromatics, and the first stream of $C_9^+$ aromatics and non-aromatics are separated from the depentanized oil via the deheptanizer, xylene tower, and extractive fractionation unit; the first stream of $C_8$ aromatics is withdrawn from the top of the xylene tower, the stream rich in $C_9$ and $C_{10}$ aromatics is withdrawn from the side line at the bottom, and $C_{11}^+$ hydrocarbons are or are not withdrawn from the bottom; the catalyst used in the selective disproportionation unit of toluene is a platinum-containing ZSM-5 molecular sieve; the catalyst used in the aromatics alkyl transfer unit is a bismuth- or molybdenum-containing macroporous zeolite catalyst; the reaction pressure in the reaction zone of the toluene selective disproportionation unit is 1–4 MPa, reaction temperature is 300–480° C., hydrogen/hydrocarbon mole ratio is 0.5–10, and weight space velocity is 0.8–8 h$^{-1}$; the feedstock used in the toluene selective disproportionation unit is a stream rich in toluene; the reaction pressure in the reaction zone of the aromatics alkyl transfer unit is 1–5 MPa, reaction temperature is 250–480° C., hydrogen/hydrocarbon mole ratio is 0.5–10, and weight space velocity is 0.8–8 h$^{-1}$; the feed to the reactor of the aromatics alkyl transfer unit contains 0–5% by weight of indan and 0–20% by weight of $C_{10}^+$ hydrocarbons.

Adjusting the amount of the stream withdrawn from the bottom of xylene tower II in the above technical solution is a way to control the average molecular weight of the feed to the SATP unit. In normal operations, $C_{11}^+$ hydrocarbons are not withdrawn from the bottom so as to produce more pX. Only when the catalyst is in the end of a operation cycle and the time is not synchronized with the time for the inspection of the plant, a part of $C_{11}^+$ hydrocarbons may be withdrawn so as to lower the average molecular weight of the feed to the SATP and thereby lower the severity of the reaction and allow the operation of the SATP unit to comply with the inspection plan of the plant.

The reaction pressure in the reaction zone of the SSTDP toluene selective disproportionation unit is 1–4 MPa, reaction temperature is 300–480° C., hydrogen/hydrocarbon mole ratio is 0.5–10, and weight space velocity is 0.8–8 h$^{-1}$. The toluene feedstock contains 90–100% by weight of toluene.

The reaction pressure in the reaction zone of the SATP unit is 1–5 MPa, reaction temperature is 250–480° C., hydrogen/hydrocarbon mole ratio is 0.5–10, and weight space velocity is 0.8–8 h$^{-1}$. The feed to the reactor of the SATP unit contains 0–5% by weight of indan and 0–20% by weight of $C_{10}^+$ hydrocarbons.

In the SATP unit of the process of the present invention, the employed bismuth-containing macroporous zeolite catalyst has the function for converting benzene and $C_9^+$ aromatics into toluene and $C_8A$ in the presence of hydrogen via alkyl transfer reaction. The macroporous zeolite may be mordenite, Beta zeolite, etc. After the toluene produced in SATP enters into the toluene selective disproportionation unit, toluene selective disproportionation reaction takes place under the action of the platinum-containing ZSM-5 catalyst, and benzene and $C_8A$ with a high pX concentration are produced. The produced benzene is used as the feed to the SATP unit, while The produced $C_8A$ with a high pX concentration is recovered by a simple one- or two-step crystallization separation and most highly pure pX product is derived and withdrawn to outside. The $C_8^+A$ after separating pX directly enters into the adsorptive and isomerization unit. Since the pX concentration in the $C_8^+A$ stream is still much higher than the thermodynamic equilibrium value, the pX concentration in $C_8A$ withdrawn from the top of xylene tower II is raised, thereby the recovery rate of pX in the pX adsorption unit is raised and the separation cost is lowered. The $C_8A$ produced in SATP enter into the adsorptive separation and isomerization unit to produce pX.

It can be seen that such a process converts all $C_6^+$ aromatics into p-xylene with a high added value. After the perfection of the performance among various units by adding a SSTDP unit and reforming the original toluene disproportionation unit into the SATP unit, the output of pX is effectively increased and the operation cost is lowered. Therefore, the process of the present invention can largely and economically produce pX.

Turning now to FIG. 3, I is the deheptanizer, II is the xylene tower II, III is the adsorptive separation and isomerization unit, IV is the SSTDP unit, V is the SATP unit, VI is the extraction fractionation unit. Depentanized oil ($C_6^+$ hydrocarbons) 4 withdrawn from the bottom of the deheptanizer of the reforming unit enters into the deheptanizer, stream 5 rich in benzene and toluene is withdrawn from the top and fed to the extractive fractionation unit. Stream 6 rich in $C_8^+A$ withdrawn from the bottom of the deheptanizer enters into xylene tower II, $C_8A$ stream 7 withdrawn from the top enters into the adsorptive separation and isomerization unit, stream 8 rich in $C_9A$ withdrawn from the side line at the bottom is fed to the SATP unit, and the bottom $C_{11}^+$ hydrocarbons stream 9 is or is not withdrawn. After the $C_8A$ entering into the adsorptive separation and isomerization unit is processed, non-aromatics (NA) 10 and p-xylene product 11 are directly withdrawn and $C_9A$-containing stream 12 and toluene stream 13 enter into xylene tower II and the SSTDP unit respectively. After entering into the SSTDP unit, toluene streams 14 and 19 are subjected to the toluene selective disproportionation reaction in the presence of hydrogen, non-aromatics 15 produced in the reaction and p-xylene 16 derived by separation are withdrawn, and $C_8^+A$ stream 22 after separating pX directly enters into the adsorptive separation and isomerization unit. Benzene stream 17 produced in SSTDP and benzene stream 18 from the extractive fractionation unit, and stream 8 rich in $C_9A$ and $C_{10}A$ from the side line at the bottom of xylene tower II enter into the SATP unit to conduct the alkyl transfer reaction in the presence of hydrogen, toluene 19 produced in the reaction enters into the SSTDP unit, the produced $C_8A$ stream 20 enters into the adsorptive separation and isomerization unit, non-aromatics 21 is withdrawn. 23 is the non-aromatics withdrawn from the extraction fractionation unit.

The main reactions involved in the process of the present invention include:

(I) SSTDP unit

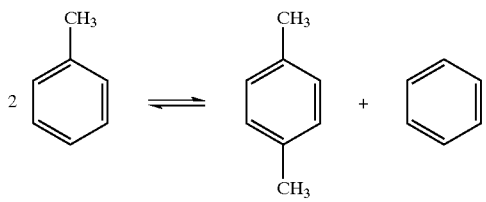

(II) SATP unit

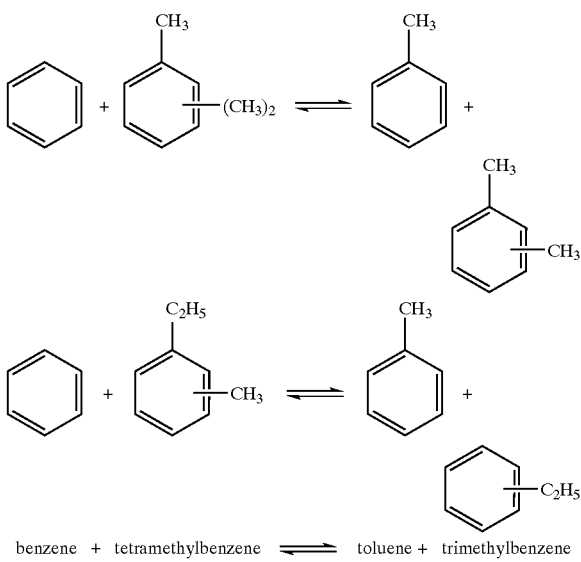

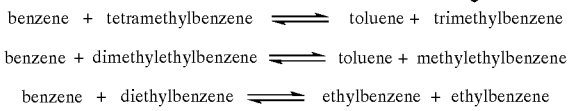

In the process of the present invention, the concept of the alkyl transfer reaction in the SATP unit differs from that of the traditional alkyl transfer reaction. The process of the present invention uses benzene and $C_9$ and higher aromatics ($C_9^+A$) as the feedstocks to produce toluene and $C_8A$ in the reaction. After simple fractionation, the derived toluene may be used as the feed to the SSTDP unit, while the derived $C_8A$ enters into the adsorptive separation and isomerization unit. The unreacted benzene and $C_9^+A$ are recycled. The toluene from the SATP unit and the extractive fractionation unit enters into the SSTDP unit to conduct the toluene selective disproportionation reaction and converts into benzene and xylene with a high concentration of p-xylene. The benzene produced in the SSTDP unit enters into the SATP unit and the produced xylene with a high concentration of p-xylene is subjected to simple crystallization separation to recover most pX, and then the residual liquid directly enters into the adsorptive separation and isomerization unit, thus the $C_9^+A$ in the residual liquid finally also enters into the SATP unit. The capacity for producing p-xylene can be greatly raised in case of an invariable scale of the reforming unit since benzene and heavy aromatics are also used as the feedstocks for producing p-xylene.

Because of the presence of a SSTDP unit having the ability to independently produce pX, the process of the present invention can increase the output of pX andco-produce a great amount of high quality nitro-grade benzene by purchasing toluene from outside. High quality benzene can also be co-produced after meeting the need of the SATP unit for benzene. Therefore, the present invention has not only a unique ability to increase the output of pX, but also a flexibility to realize the diversification of the product.

The present invention will be further described below by the examples.

EXAMPLES 1–7

The performance for the alkyl transfer reaction between benzene and $C_9^+A$ was examined in the presence of hydrogen using a fixed-bed reactor. The reactor was made from stainless steel tube with an inner diameter of φ25 mm and a length of 1000 mm. Glass beads of φ3 mm were filled both above and beneath the catalyst bed for distributing and supporting. The reactor was loaded with 20 g of a bismuth-containing macroporous zeolite catalyst. The aromatics feedstock passed through the catalyst bed from top to bottom after mixing with hydrogen to conduct the alkyl transfer reaction between benzene and $C_9^+A$ yielding toluene and $C_8A$.

Benzene and $C_9^+A$ in the feed were from a petrochemical aromatics integrated device, and the $H_2$ was electrolyzed hydrogen treated via dehydration for drying. The reaction results are shown in Table 1.

an inner diameter of φ25 mm, a length of 1000 mm. Glass beads of φ3 mm were filled both above and beneath the catalyst bed for distributing and supporting. The reactor was loaded with 20 g of a platinum-containing ZSM-5 molecular sieve catalyst. Toluene passed through the catalyst bed from top to bottom after mixing with hydrogen to conduct the toluene selective disproportionation reaction yielding benzene and $C_8A$ with a high concentration of p-xylene.

The toluene feedstock was from a petrochemical aromatics integrated device, and the $H_2$ was electrolyzed hydrogen treated via dehydration for drying. The reaction temperature was 420° C., reaction pressure was 1.5 MPa, space velocity was 4.0 $h^{-1}$, and hydrogen/hydrocarbon mole ratio was 3.0. The results are shown in Table 2.

TABLE 2

Result of toluene selective disproportionation reaction

| | Component | | | | | | |
|---|---|---|---|---|---|---|---|
| | NA | Ben | Tol | pX | $C_8A^*$ | $C_9^+A$ | Σ |
| Composition, wt % | 1.74 | 14.05 | 69.95 | 11.62 | 2.02 | 0.62 | 100.00 |

Note:
$C_8A^*$ denotes the other $C_8A$ except pX.

The content of pX in xylene was 89%, basically identical with the reported datum of the MSTDP process employed in industry.

TABLE 1

Analysis of feedstock and product compositions in alkyl transfer reaction between benzene and $C_9^+A$ (1–7)

| | | Example | | | | | | |
|---|---|---|---|---|---|---|---|---|
| | | 1 | 2 | 3 | 4 | 5 | 6 | 7 |
| Main active component of the catalyst* | | A | B | B | A | A | B | B |
| Reaction temperature, ° C. | | 325 | 365 | 440 | 460 | 410 | 420 | 380 |
| Reaction pressure, MPa | | 1.5 | 1.5 | 4 | 4 | 2.5 | 3 | 3 |
| Weight space velocity, $h^{-1}$ | | 0.8 | 1.3 | 4.5 | 6 | 3.5 | 3 | 2 |
| $H_2$/HCs mole ratio | | 3 | 2 | 8.5 | 10 | 5 | 6 | 6 |
| Feed composition, wt % | NA | 0.01 | 0.01 | 0.10 | 0.10 | 0.01 | 0.01 | 0.01 |
| | Ben | 73.98 | 73.98 | 64.00 | 64.00 | 50.91 | 50.91 | 66.62 |
| | Tol | 0.01 | 0.01 | 0.19 | 0.19 | 0.01 | 0.01 | 0.01 |
| | $C_8A$ | 0.26 | 0.26 | 0.29 | 0.29 | 0.26 | 0.26 | 0.26 |
| | $C_9A$ | 19.13 | 19.13 | 22.01 | 22.01 | 34.22 | 34.22 | 23.38 |
| | IND | 0.61 | 0.61 | 3.49 | 3.49 | 1.56 | 1.56 | 0.30 |
| | $C_{10}^+$HCs | 6.00 | 6.00 | 9.92 | 9.92 | 13.03 | 13.03 | 9.43 |
| | Σ | 100.00 | 100.00 | 100.00 | 100.00 | 100.00 | 100.00 | 100.00 |
| Product composition, | NA | 2.51 | 3.01 | 4.01 | 5.21 | 6.09 | 5.6 | 2.94 |
| | Ben | 49.57 | 50.31 | 40.48 | 40.96 | 30.52 | 29.53 | 39.30 |
| | Tol | 25.72 | 25.33 | 27.91 | 25.31 | 29.05 | 30.91 | 30.01 |
| | $C_8A$ | 13.11 | 12.67 | 14.96 | 14.42 | 17.43 | 18.55 | 16.21 |
| | $C_9A$ | 5.86 | 5.06 | 6.21 | 8.03 | 9.57 | 8.39 | 5.76 |
| | $C_{10}^+A$ | 3.23 | 3.62 | 6.43 | 6.07 | 7.34 | 7.02 | 5.78 |
| | Σ | 100.00 | 100.00 | 100.00 | 100.00 | 100.00 | 100.00 | 100.00 |

Note:
A denotes bismuth-containing mordenite;
B denotes bismuth-containing β-zeolite.

It can be seen from Examples 1–7 that benzene and $C_9^+A$ in the feedstock converted to toluene and $C_8A$ after reaction.

EXAMPLE 8

The toluene selective disproportionation reaction was conducted in the presence of hydrogen using a fixed-bed reactor. The reactor was made from stainless steel tube with

COMPARATIVE EXAMPLE 1

The flow rate of the reformed depentanized oil $C_6A$–$C_{10}^+$ hydrocarbon stream from a typical aromatics integrated device was taken as a basic datum (see Table 3) to examine the capacity of the present invention for producing pX.

TABLE 3

Composition and flow rate of aromatics in the reformed depentanized oil

| | Component | | | | | |
|---|---|---|---|---|---|---|
| | Ben | Tol | $C_8A$ | $C_9A$ | $C_{10}^+$ HCs | Σ |
| Composition, W/T | 44.4 | 100.0 | 132.6 | 115.9 | 24.9 | 417.8 |

Note:
the flow rate of Tol = 100 W/T as a base, W/T denotes unit weight/unit time.

Based on the aforesaid process flow of the present invention and the composition and flow rate of aromatics (fresh feedstock) in Table 3 as well as the results of the toluene selective disproportionation reaction in Example 8, simulation calculation was conducted on computer, and the feed and withdrawal data of the SSTDP unit and SATP unit are shown in Table 4.

In the process of the present invention, when the fresh feed (aromatics in reformed depentanized oil) amounted 417.8 W/T (see Table 3), the withdrawal of p-xylene from SSTDP was 117.4 W/T, the total amount of $C_8A$ entering into the adsorptive separation isomerization unit was:

132.6+20.4+109.9=262.9 (W/T)

From calculation, the mole ratio of the total fresh feed aromatics (i.e. the reacted aromatics) to the withdrawn aromatics in the whole device was 1.13, the feed aromatics/withdrawn aromatics mole ratio in the SATP unit was 1.10, and there was no isomerization during the reaction. The computer simulation for the feed and withdrawal in various unit of the process flow of the present invention is reasonable.

The amounts of various products produced after 262.9 (W/T) of $C_8A$ entered into the adsorptive separation and isomerization unit are shown in Table 5.

TABLE 4

Material balance of the process of the present invention

| Component | | Reformed depentanized oil | SSTDP unit | SATP unit |
|---|---|---|---|---|
| Fresh feed, W/T | NA | / | / | / |
| | Ben | 44.4 | / | 186.3 |
| | Tol | 100.0 | 303.5 | / |

TABLE 4-continued

Material balance of the process of the present invention

| Component | | Reformed depentanized oil | SSTDP unit | SATP unit |
|---|---|---|---|---|
| | $C_9A^*$ | 115.9 | / | 122.2 |
| | $C_{10}^+A$ | 24.9 | / | 24.9 |
| | Σ | 285.2 | 303.5 | 333.4 |
| Product withdrawal, W/T | NA | / | 17.6 | 20.0 |
| | Ben | / | 141.9 | / |
| | Tol | / | / | 203.5 |
| | pX | 132.6 | 117.4 | 109.9 |
| | $C_8A^*$ | | 20.4 | |
| | $C_9A$ | / | 6.3 | / |
| | $C_{10}^+A$ | / | / | / |
| | Σ | 132.6 | 303.6 | 333.4 |

Note:
A small amount of IDN is incorporated into $C_9A$ and $C_8A^*$ denotes the other $C_8$ aromatics except pX.

TABLE 5

Amount of various products converted from $C_8A^*$ (unit: W/T)

| | Component | | | | |
|---|---|---|---|---|---|
| | NA | pX | Tol | $C_9^+A$ | Σ |
| Output | 23.7 | 226.1 | 2.6 | 10.5 | 262.9 |

Note:
The yield of pX was 86% by weight, that of non-aromatics (NA) was 9% by weight, that of toluene was 1% by weight, and that of $C_{10}^+A$ was 4% by weight when pX was finally withdrawn after the adsorptive separation and isomerization of $C_8A$; The same below.

Therefore, after various aromatics feedstocks in Table 3 were reacted, the present invention could produce pX:
226.1+117.4=343.5 (W/T)

Besides, there are still 2.6 W/T of toluene and 10.5 W/T of $C_9^+A$ that can be used to produce pX (see Table 5).

On this basis, a series of tests were made in laboratory, the derived data for Example 7 agree with the simulated data of the fresh feed and the product withdrawal in the SATP unit.

In summary, the process of the present invention can produce 343.5 W/T of pX after the aromatics feedstocks shown in Table 3 have been reacted.

COMPARATIVE EXAMPLE 2

The flow rate of the reformed depentanized oil $C_6A$–$C_{10}A$ stream from the typical aromatics integrated device in Table 3 was also taken as the basic datum to examine the capacity of the traditional aromatics integrated device containing toluene disproportionation and alkyl transfer unit for producing pX. The data of the materials are shown in Table 6.

TABLE 6

The output of pX in an aromatics integrated device adopting toluene disproportionation and alkyl transfer process (unit: W/T)

| Component | Fresh feed | Processing mode | Product withdrawal in Mode I | Product withdrawal in Mode II | Product withdrawal in Mode III* | Product withdrawal from integrated device |
|---|---|---|---|---|---|---|
| NA | / | / | / | 11.9 | 23.6 | 35.5 |
| Ben | 44.4 | Withdrawn to outside (I) | 44.4 | / | 45.8 | 90.2 |
| PX | / | / | / | 114.0 | 130.1 | 244.1 |
| $C_8A$ | 132.6 | To adsorptive separation and isomerization (II) | / | / | / | / |
| Tol | 100.0 | Typical Toluene | / | 1.3 | 1.5 | 2.8 |

TABLE 6-continued

The output of pX in an aromatics integrated device adopting toluene
disproportionation and alkyl transfer process (unit: W/T)

| Component | Fresh feed | Processing mode | Product withdrawal in Mode I | Product withdrawal in Mode II | Product withdrawal in Mode III* | Product withdrawal from integrated device |
|---|---|---|---|---|---|---|
| $C_9A$ | 115.9 | disproportionation (III). | / | 5.3 | 6.0 | 11.3 |
| $C_{10}^+A$ | 24.9 | Withdrawn to outside (I) | 24.9 | / | 8.9 | 33.8 |
| Σ | 417.8 | / | 69.3 | 132.5 | 215.9 | 417.7 |

Note:
*$C_8A$ produced by toluene disproportionation and alkyl transfer is calculated as pX and other aromatics according to processing mode II.

The "fresh feed" in the above table denotes the flow rates of various components in the reformed depentanized oil from upstream; the "processing mode" denotes the treating way of various components; the "product withdrawal from integrated device" denotes the amounts of the final products after the fresh feedstocks are treated. The calculation method for processing mode (II) is the same as Table 5. When using processing mode (III), i.e. the traditional toluene disproportionation and alkyl transfer process, the yield of the non-aromatics was 4.62% by weight, that of benzene was 21.21% by weight, that of $C_8A$ was 70.05% by weight, and that of $C_{10}$ hydrocarbons was 4.12% by weight.

The produced 2.8 W/T of toluene and 11.3 W/T of $C_9A$ can convert into 8.5 W/T of p-xylene at most, i.e. the maximum yield of p-xylene via the typical toluene disproportionation and alkyl transfer process was:

244.1+8.5=252.6 W/T.

It can be seen from above results that the present invention has overcome the shortcomings present in the prior arts of the production of a large amount of benzene as a by-product and low content of $C_{10}^+$ heavy aromatics in the feedstock in the production of pX, and provided a completely new and more economical process for producing p-xylene. Furthermore, for a typical aromatics integrated device, the output of p-xylene can be markedly increased in case of the same amount of the feedstock by making full use of the existing units and technique since benzene is also used as a feedstock for producing p-xylene. It can be seen from Comparative Examples 1 and 2 that compared to the typical toluene disproportionation and alkyl transfer process, the process of the present invention can increase the output of p-xylene by 36%.

What we claim is:

1. A process for producing p-xylene comprising:
   a) separating a depentanized oil rich in benzene, toluene, $C_8$ aromatics, and $C_9^+$ aromatics into a first stream of benzene, a first stream of toluene, a first stream of $C_8$ aromatics, and a first stream of $C_9^+$ aromatics;
   b) 1) introducing the first stream of toluene and a second stream of toluene from an aromatics alkyl transfer unit into a toluene selective disproportionation unit to conduct toluene selective disproportionation reaction in the presence of hydrogen, to produce a second stream of benzene and a second stream of $C_8$ aromatics rich in p-xylene; and
   2) separating the second stream of $C_8$ aromatics rich in p-xylene into a first highly pure p-xylene product and a stream of remaining $C_8$ aromatics;
   c) introducing at least a part of the first and the second stream of benzene and the first stream of $C_9^+$ aromatics into the aromatics alkyl transfer unit to conduct aromatics alkyl transfer reaction in the presence of hydrogen, to produce the second stream of toluene and a third stream of $C_8$ aromatics; and
   d) introducing the first stream of $C_8$ aromatics, the stream of remaining $C_8$ aromatics and the third stream of $C_8$ aromatics into a molecular sieve adsorptive separation and $C_8$ aromatics isomerization unit to produce a second p-xylene product.

2. The process of claim 1 wherein a part of the second stream of toluene obtained in step of c) is withdrawn as a product.

3. The process of claim 1 wherein the separating in step of b) 2) is conducted by method of crystallization separation.

4. The process of claim 1 wherein the separating in step b) 2) is conducted in the molecular sieve adsorptive separation and $C_8$ aromatics isomerization unit employed in step d) together with the separation of the first stream of $C_8$ aromatics and the third stream of $C_8$ aromatics.

5. The process of claim 1 wherein the depentanized oil rich in aromatics is from a reforming unit.

6. The process of claim 1 wherein the separating of the depentanized oil in step a) is conducted in a deheptanizer, a xylene tower, and an extractive fractionation unit.

7. The process of claim 4 wherein the first stream of $C_8$ aromatics is withdrawn from the top of the xylene tower, the first stream of $C_9^+$ aromatics is withdrawn from a side line near the bottom of the xylene tower.

8. The process of claim 4 further comprising withdrawing $C_{11}^+$ hydrocarbons from the bottom of the xylene tower.

9. The process of claim 1 wherein the toluene selective disproportionation unit employs a ZSM-5 molecular sieve catalyst comprising platinum.

10. The process of claim 1 wherein the aromatics alkyl transfer unit employs a macroporous zeolite catalyst.

11. The process of claim 10 wherein the macroporous zeolite catalyst comprises bismuth.

12. The process of claim 1 wherein the reaction zone of the toluene selective disproportionation unit has a pressure of 1–4 MPa, a temperature of 300–480° C., a hydrogen and hydrocarbon mole ratio of 0.5–10, and a weight space velocity of 0.8–8 $h^{-1}$.

13. The process of claim 1 wherein the feedstock of the toluene selective disproportionation unit is a stream rich in toluene.

14. The process of claim 1 wherein the reaction zone of the aromatics alkyl transfer unit has a pressure of 1–5 MPa, a temperature of 250–480° C., a hydrogen and hydrocarbon mole ratio of 0.5–10, and a weight space velocity of 0.8–8 $h^{-1}$.

15. The process of claim 1 wherein the feedstock of the aromatics alkyl transfer unit comprises 0–5% by weight of indan and 0–20% by weight of $C_{10}^+$ hydrocarbons.

* * * * *